(12) United States Patent
Yumbe

(10) Patent No.: US 11,627,864 B2
(45) Date of Patent: Apr. 18, 2023

(54) MEDICAL IMAGE PROCESSING APPARATUS, ENDOSCOPE SYSTEM, AND METHOD FOR EMPHASIZING REGION OF INTEREST

(71) Applicant: FUJIFILM Corporation, Tokyo (JP)

(72) Inventor: Hirona Yumbe, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/206,136

(22) Filed: Mar. 19, 2021

(65) Prior Publication Data
US 2021/0204794 A1 Jul. 8, 2021

Related U.S. Application Data

(63) Continuation of application No. PCT/JP2019/037100, filed on Sep. 20, 2019.

(30) Foreign Application Priority Data

Sep. 26, 2018 (JP) .............................. JP2018-180054

(51) Int. Cl.
| | | |
|---|---|---|
| *A61B 1/00* | (2006.01) | |
| *A61B 1/05* | (2006.01) | |
| *A61B 1/06* | (2006.01) | |
| *G09G 5/02* | (2006.01) | |
| *G09G 5/38* | (2006.01) | |
| *H04N 7/18* | (2006.01) | |
| *G06V 10/25* | (2022.01) | |
| *G06T 3/40* | (2006.01) | |

(Continued)

(52) U.S. Cl.
CPC ........ *A61B 1/00006* (2013.01); *A61B 1/0005* (2013.01); *A61B 1/000094* (2022.02);
(Continued)

(58) Field of Classification Search
None
See application file for complete search history.

(56) References Cited

U.S. PATENT DOCUMENTS

2003/0035051 A1* 2/2003 Cho ...................... G01S 3/7865
348/169
2007/0232863 A1 10/2007 Miyake et al.
(Continued)

FOREIGN PATENT DOCUMENTS

| JP | 2007222239 | 9/2007 |
|---|---|---|
| JP | 2011254936 | 12/2011 |

(Continued)

OTHER PUBLICATIONS

"Search Report of Europe Counterpart Application", dated Oct. 18, 2021, p. 1-p. 6.

(Continued)

*Primary Examiner* — Richard T Torrente
(74) *Attorney, Agent, or Firm* — JCIPRNET

(57) ABSTRACT

A processor device includes an image signal acquiring unit, an image processing unit, and a display control unit. The image signal acquiring unit acquires a digital image signal corresponding to an observation mode from an endoscope. The image processing unit includes a region-of-interest-detection-mode image processing unit. The display control unit sets an emphasized region having a larger area than a region of interest and including the region of interest, displays the emphasized region in a manner of emphasized display, and determines whether or not to change setting of the emphasized region in accordance with an amount of variation of the region of interest.

11 Claims, 11 Drawing Sheets

(51) Int. Cl.
  *G06T 7/00* (2017.01)
  *G06T 7/11* (2017.01)
  *H04N 23/56* (2023.01)
  *G06V 10/764* (2022.01)
  *G06V 10/82* (2022.01)
  *G06V 10/143* (2022.01)
  *H04N 23/50* (2023.01)

(52) U.S. Cl.
  CPC .............. *A61B 1/05* (2013.01); *A61B 1/0684* (2013.01); *G06T 3/40* (2013.01); *G06T 7/0012* (2013.01); *G06T 7/11* (2017.01); *G06V 10/143* (2022.01); *G06V 10/25* (2022.01); *G06V 10/764* (2022.01); *G06V 10/82* (2022.01); *G09G 5/02* (2013.01); *G09G 5/38* (2013.01); *H04N 7/183* (2013.01); *H04N 23/56* (2023.01); *G06V 2201/03* (2022.01); *G09G 2354/00* (2013.01); *G09G 2380/08* (2013.01); *H04N 23/555* (2023.01)

(56) References Cited

U.S. PATENT DOCUMENTS

| | | | | |
|---|---|---|---|---|
| 2011/0254937 | A1* | 10/2011 | Yoshino | A61B 1/0655 348/E7.085 |
| 2011/0301443 | A1 | 12/2011 | Yamaguchi et al. | |
| 2012/0218394 | A1 | 8/2012 | Yoshino et al. | |
| 2013/0218978 | A1* | 8/2013 | Weinstein | H04L 65/401 709/205 |
| 2015/0279021 | A1* | 10/2015 | Wu | G06T 7/277 382/103 |
| 2016/0287214 | A1* | 10/2016 | Ralovich | A61B 8/5215 |
| 2018/0098690 | A1 | 4/2018 | Iwaki | |
| 2018/0325604 | A1* | 11/2018 | Atarot | A61B 1/3132 |
| 2019/0069757 | A1 | 3/2019 | Iwaki | |

FOREIGN PATENT DOCUMENTS

| | | |
|---|---|---|
| JP | 5802364 | 10/2015 |
| JP | 6120762 | 4/2017 |
| WO | 2017203560 | 11/2017 |

OTHER PUBLICATIONS

"International Search Report (Form PCT/ISA/210) of PCT/JP2019/037100," dated Nov. 19, 2019, with English translation thereof, pp. 1-5.

"Written Opinion of the International Searching Authority (Form PCT/ISA/237) of PCT/JP2019/037100," dated Nov. 19, 2019, with English translation thereof, pp. 1-6.

* cited by examiner

MEDICAL IMAGE PROCESSING APPARATUS, ENDOSCOPE SYSTEM, AND METHOD FOR EMPHASIZING REGION OF INTEREST

CROSS-REFERENCE TO RELATED APPLICATIONS

This application is a Continuation of PCT International Application No. PCT/JP2019/037100 filed on 20 Sep. 2019, which claims priority under 35 U.S.C § 119(a) to Japanese Patent Application No. 2018-180054 filed on 26 Sep. 2018. The above application is hereby expressly incorporated by reference, in its entirety, into the present application.

BACKGROUND OF THE INVENTION

1. Field of the Invention

The present invention relates to a medical image processing apparatus, an endoscope system, and a method for operating the medical image processing apparatus that are for detecting a region of interest such as a lesion portion.

2. Description of the Related Art

In the medical field, image diagnosis is performed for diagnosing a disease of a patient, performing follow-up, or the like by using a medical image such as an endoscopic image, an X-ray image, a computed tomography (CT) image, or a magnetic resonance (MR) image. A medical doctor or the like determines a course of treatment on the basis of such image diagnosis.

In recent years, image diagnosis using medical images has been employing a way of analyzing a medical image and automatically detecting a region of interest to be carefully observed, such as a lesion or a tumor in an organ. In particular, execution of machine learning such as deep learning dramatically increases the accuracy of detecting a region of interest.

JP5802364B (corresponding to US2012/0218394A1) describes a medical image processing apparatus that performs, in a case where a region of interest such as a lesion portion is detected from a medical image, image processing on the basis of a detection result. In the medical image processing apparatus described in JP5802364B, a region including pixels in which a region of interest has been detected is set as an emphasized region, and the display manner of the emphasized region is made different. For example, the region of interest is emphasized by performing a color conversion process of converting the color of the pixels in the emphasized region to a target color. When the position or size of the detected region of interest changes, the emphasized region also changes, and the position or size of emphasized display in the medical image is changed.

JP6120762B describes a medical image processing apparatus that displays, in a case where a region of interest such as a lesion portion is detected from any one of four regions obtained by dividing a medical image, a partial display frame around the region in the four regions from which the region of interest has been detected.

SUMMARY OF THE INVENTION

In the medical image processing apparatus described in JP5802364B, however, when the position or size of a region of interest in a medical image changes, the position or size of emphasized display also changes accordingly. Thus, flicker is likely to occur within a display screen, which disturbs observation performed by a medical doctor.

In the medical image processing apparatus described in JP6120762B, in a case where a region of interest is detected, flicker does not occur within a display screen because a display frame is displayed around the display screen. However, the display frame indicates the position of the region of interest only roughly, and thus the exact position thereof is not clear.

An object of the present invention is to provide a medical image processing apparatus, an endoscope system, and a method for operating the medical image processing apparatus that enable an exact position of a region of interest to be recognized and that are capable of preventing flicker in a display screen.

A medical image processing apparatus of the present invention includes a medical image acquiring unit, a region-of-interest detecting unit, and a display control unit. The medical image acquiring unit acquires a medical image through imaging of an observation target. The region-of-interest detecting unit detects a region of interest in the observation target from the medical image acquired by the medical image acquiring unit. The display control unit sets an emphasized region having a larger area than the region of interest and including the region of interest and displays the emphasized region in the medical image in a manner of emphasized display, the display control unit determining whether or not to change setting of the emphasized region in accordance with an amount of variation of the region of interest in the medical image.

Preferably, the display control unit may set a reference region on an outer side of the region of interest and an inner side of the emphasized region when setting the emphasized region, and may reset the emphasized region and the reference region in a case where at least a part of the region of interest has shifted to an outside of the reference region.

Preferably, in a case of resetting the emphasized region and the reference region after setting the emphasized region and the reference region, the display control unit may cause a position of the emphasized display after resetting to be different from a position of the emphasized display before resetting.

Preferably, in a case of resetting the emphasized region and the reference region after setting the emphasized region and the reference region, the display control unit may cause the emphasized display after resetting to be enlarged relative to the emphasized display before resetting.

Preferably, in a case where an enlargement ratio of an area of the region of interest exceeds a first threshold value after the emphasized region is set, the display control unit may reset the emphasized region to cause the emphasized display after resetting to be enlarged relative to the emphasized display before resetting.

Preferably, in a case where the enlargement ratio of the area of the region of interest exceeds a second threshold value greater than the first threshold value after the emphasized region is set, the display control unit may make a change to reduce an area of a figure to be superimposed on the medical image for the emphasized display.

Preferably, the display control unit may determine representative coordinates of the region of interest detected by the region-of-interest detecting unit, and may reset a position of the emphasized region in a case where a position of the representative coordinates has moved by a threshold value or more.

Preferably, the display control unit may cause a frame-shaped figure superimposed on the emphasized region to be displayed for emphasized display.

Preferably, the display control unit may change a color of the emphasized region to a color different from a color of an other portion of the medical image for emphasized display.

Preferably, in a case where the enlargement ratio exceeds the second threshold value, the display control unit may cause an icon or a band-shaped figure to be displayed outside a part to be observed in the medical image for the emphasized display.

An endoscope system of the present invention includes a light source device, an endoscope, a medical image acquiring unit, a region-of-interest detecting unit, a display control unit, and a display device. The light source device emits illumination light for illuminating an observation target. The endoscope has an imaging device that performs imaging of the observation target illuminated with the illumination light. The medical image acquiring unit acquires a medical image, the medical image being obtained through imaging of the observation target performed by the imaging device. The region-of-interest detecting unit detects a region of interest in the observation target from the medical image acquired by the medical image acquiring unit. The display control unit sets an emphasized region having a larger area than the region of interest and including the region of interest and displays the emphasized region in the medical image in a manner of emphasized display. The display control unit determines whether or not to change setting of the emphasized region in accordance with an amount of variation of the region of interest in the medical image. The display device displays the medical image to which the emphasized display is applied.

A method for operating a medical image processing apparatus of the present invention includes a step of, with a medical image acquiring unit, acquiring a medical image, the medical image being obtained through imaging of an observation target performed by an imaging device; a step of, with a region-of-interest detecting unit, detecting a region of interest in the observation target from the medical image acquired by the medical image acquiring unit; a step of, with a display control unit, setting an emphasized region having a larger area than the region of interest and including the region of interest; a step of, with the display control unit, displaying the emphasized region in the medical image in a manner of emphasized display; and a step of, with the display control unit, determining whether or not to change setting of the emphasized region in accordance with an amount of variation of the region of interest in the medical image.

According to the present invention, it is possible to recognize an exact position of a region of interest and prevent flicker in a display screen.

DESCRIPTION OF THE PREFERRED EMBODIMENTS

First Embodiment

Figure 1:
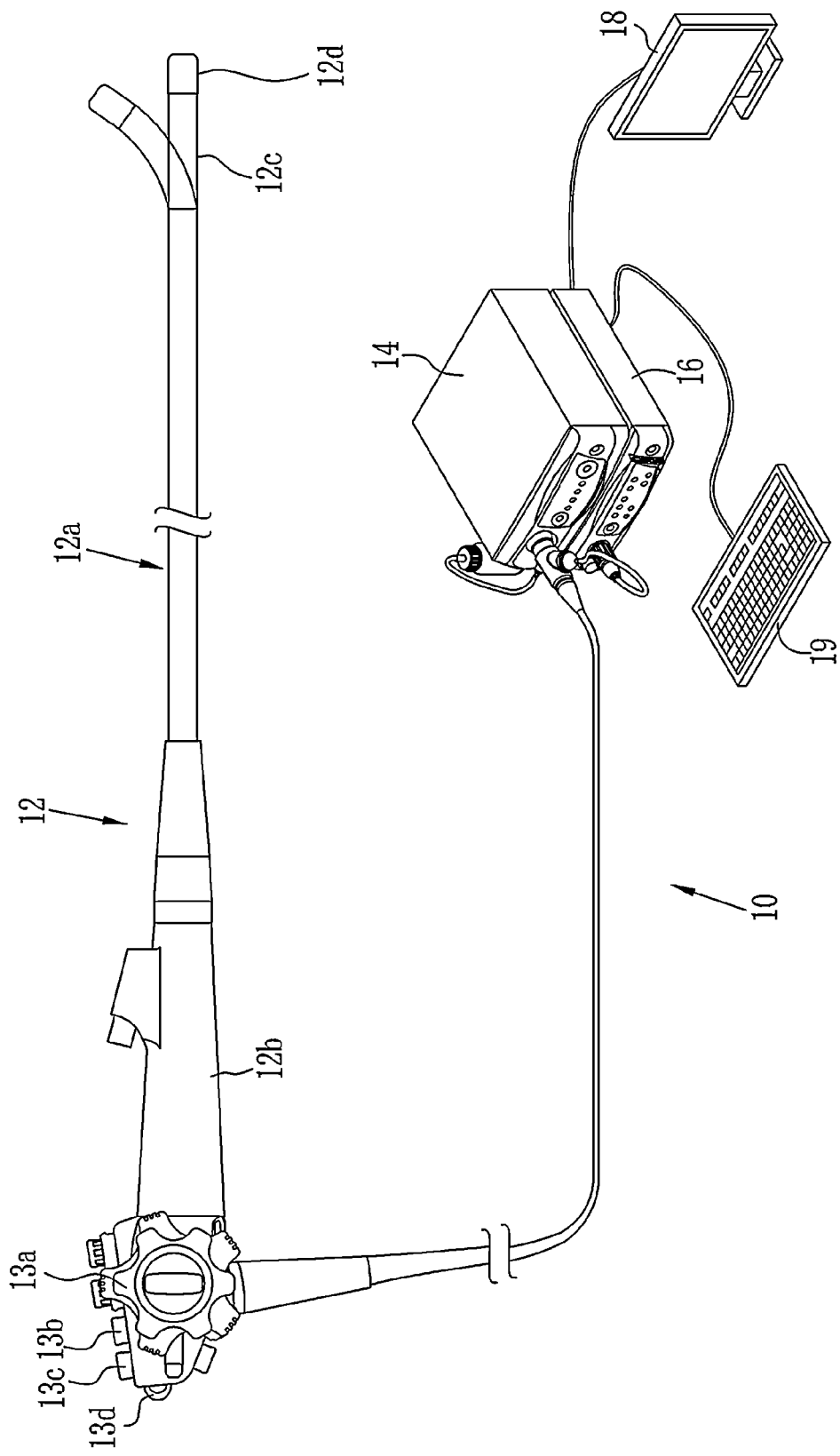
FIG. 1 is an external appearance diagram of an endoscope system.

As illustrated in FIG. 1, an endoscope system 10 has an endoscope 12, a light source device 14, a processor device 16, a monitor 18 (display device), and a console 19. The endoscope 12 is optically connected to the light source device 14 and is electrically connected to the processor device 16. The endoscope 12 has an insertion section 12a to be inserted into a subject, an operation section 12b provided at a base end portion of the insertion section 12a, and a bending portion 12c and a distal end portion 12d that are provided on a distal end side of the insertion section 12a. Operating of an angle knob 13a of the operation section 12b causes the bending portion 12c to perform a bending operation. The bending operation causes the distal end portion 12d to be directed in a desired direction.

The distal end portion 12d has, on the distal end surface thereof, an illumination window, an observation window, an air/water supply nozzle, and a forceps port (any of them is not illustrated). The illumination window is for irradiating an observation portion with illumination light. The observation window is for capturing light from the observation portion.

The air/water supply nozzle is for washing the illumination window and the observation window. The forceps port is for performing various treatments by using a treatment tool such as forceps or an electric scalpel.

The operation section 12b is provided with, in addition to the angle knob 13a, a still image acquiring unit 13b to be used for an operation of acquiring a still image, a mode switching unit 13c to be used for an operation of switching an observation mode, and a zoom operation unit 13d to be used for an operation of changing zoom magnification. The still image acquiring unit 13b is capable of performing a freeze operation of displaying a still image of an observation target on the monitor 18 and a release operation of storing a still image in storage.

The endoscope system 10 has a normal mode, a special mode, and a region-of-interest detection mode as observation modes. When the observation mode is the normal mode, normal light generated by combining light beams of a plurality of colors at a light amount ratio Lc for the normal mode is emitted. When the observation mode is the special mode, special light generated by combining light beams of a plurality of colors at a light amount ratio Ls for the special mode is emitted.

When the observation mode is the region-of-interest detection mode, illumination light for the region-of-interest detection mode is emitted. In this embodiment, normal light is emitted as the illumination light for the region-of-interest detection mode. Alternatively, special light may be emitted.

The processor device 16 is electrically connected to the monitor 18 and the console 19. The monitor 18 outputs and displays an image of an observation target, information accompanying the image, and so forth. The console 19 functions as a user interface that receives an input operation for designating a region of interest (ROI), setting a function, or the like.

Figure 2:
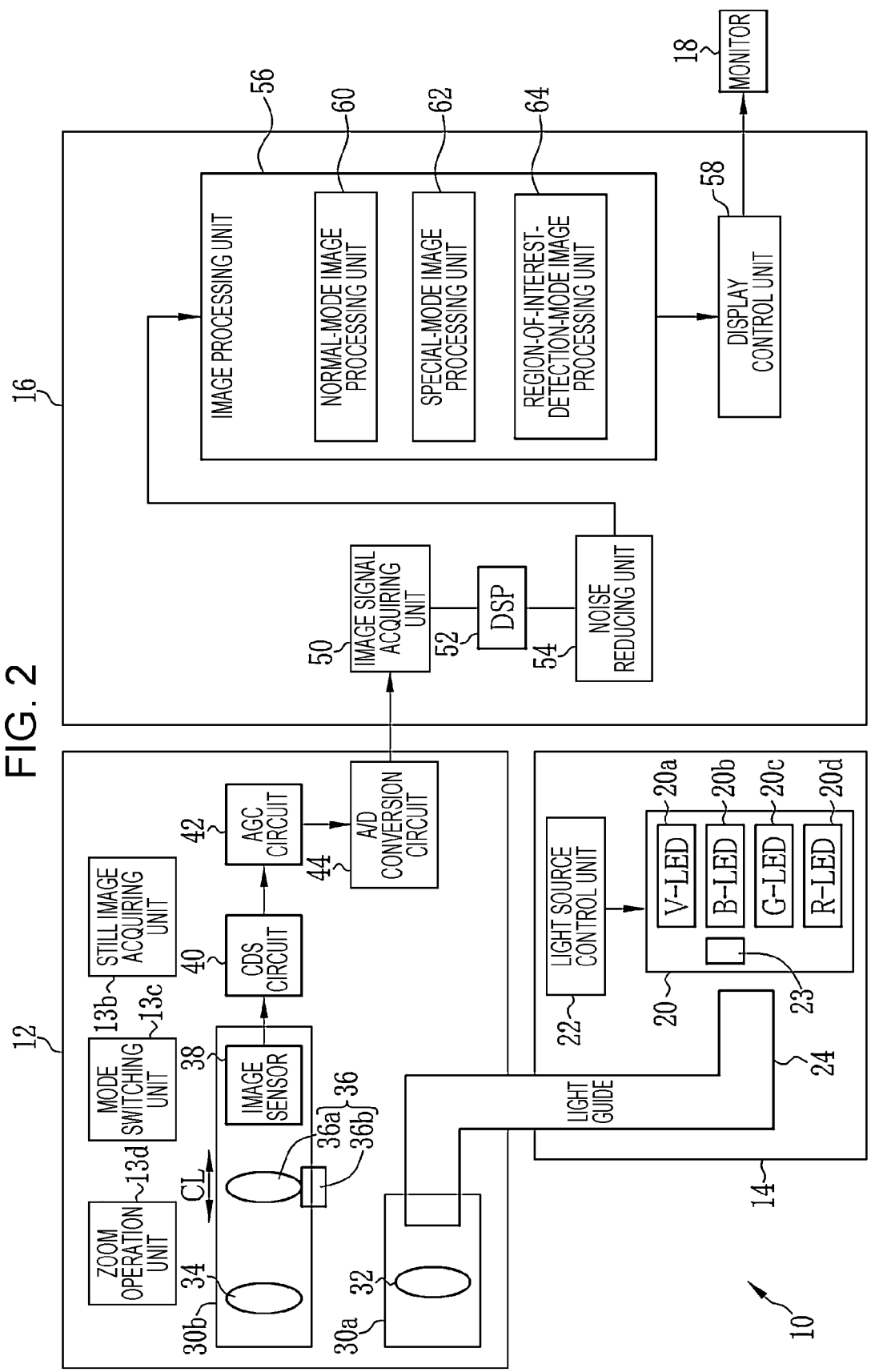
FIG. 2 is a block diagram illustrating functions of the endoscope system according to a first embodiment including a plurality of LED light sources.

As illustrated in FIG. 2, the light source device 14 includes a light source unit 20 that emits illumination light to be used to illuminate an observation target, and a light source control unit 22 that controls the light source unit 20. The light source unit 20 is a semiconductor light source, such as light emitting diodes (LEDs) of a plurality of colors. The light source control unit 22 turns ON/OFF the LEDs or the like and adjusts driving currents and driving voltages for the LEDs or the like, thereby controlling the amount of illumination light to be emitted. In addition, the light source control unit 22 controls the wavelength range of the illumination light by, for example, changing an optical filter.

Figure 3:
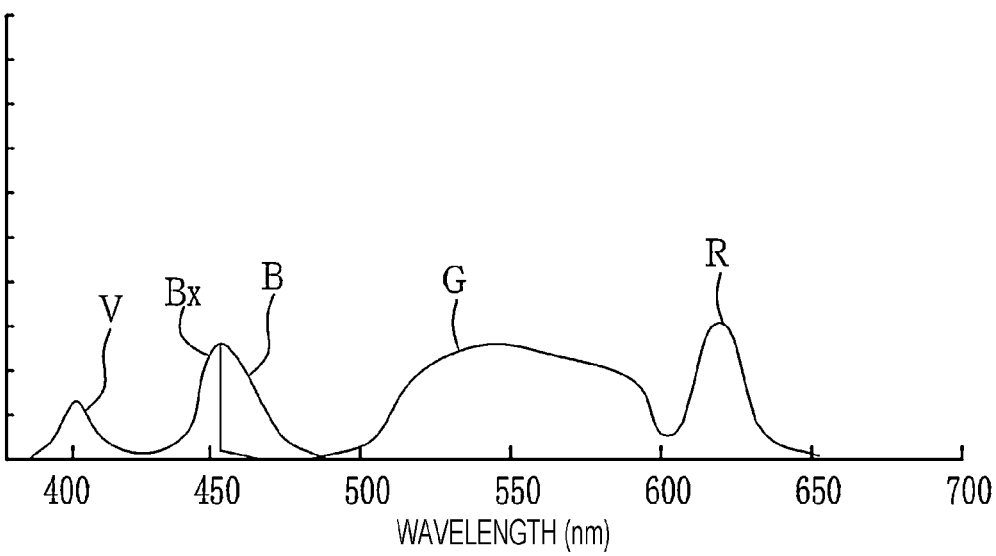
FIG. 3 is a graph illustrating a spectrum of violet light V, blue light B, blue light Bx, green light G, and red light R.

In the first embodiment, the light source unit 20 has LEDs of four colors: a violet light emitting diode (V-LED) 20a; a blue light emitting diode (B-LED) 20b; a green light emitting diode (G-LED) 20c; and a red light emitting diode (R-LED) 20d, and a wavelength cut filter 23. As illustrated in FIG. 3, the V-LED 20a emits violet light V in a wavelength range of 380 nm to 420 nm.

The B-LED 20b emits blue light B in a wavelength range of 420 nm to 500 nm. Of the blue light B emitted by the B-LED 20b, at least the longer wavelength side with respect to a peak wavelength of 460 nm is cut off by the wavelength cut filter 23. Accordingly, blue light Bx that has passed through the wavelength cut filter 23 is in a wavelength range of 420 nm to 460 nm. The light in the wavelength range on the longer wavelength side with respect to 460 nm is cut off because the light in the wavelength range on the longer wavelength side with respect to 460 nm is a factor in decreasing the contrast of blood vessels as an observation target. The wavelength cut filter 23 may decrease the amount of light in the wavelength range on the longer wavelength side with respect to 460 nm instead of cutting off the light in the wavelength range on the longer wavelength side with respect to 460 nm.

The G-LED 20c emits green light G in a wavelength range of 480 nm to 600 nm. The R-LED 20d emits red light R in a wavelength range of 600 nm to 650 nm. The light emitted by each of the LEDs 20a to 20d may have a center wavelength and a peak wavelength that are identical to or different from each other.

The light source control unit 22 controls ON/OFF of each of the LEDs 20a to 20d and the amount of light emission in an ON state independently from each other, thereby adjusting the emission timing, emission period, amount of light, and spectrum of illumination light. The ON/OFF control by the light source control unit 22 varies according to an observation mode. A reference brightness can be set by a brightness setting unit of the light source device 14, the console 19, or the like.

Figure 4:
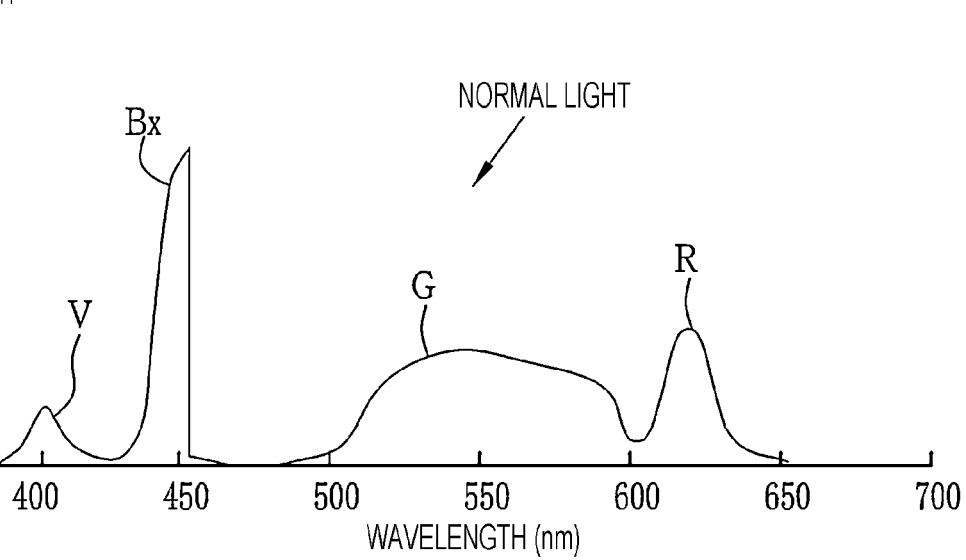
FIG. 4 is a graph illustrating a spectrum of normal light according to the first embodiment.

In the normal mode or the region-of-interest detection mode, the light source control unit 22 turns on all of the V-LED 20a, the B-LED 20b, the G-LED 20c, and the R-LED 20d. At this time, as illustrated in FIG. 4, the light amount ratio Lc among the violet light V, the blue light Bx, the green light G, and the red light R is set such that the peak intensity of the blue light Bx is higher than each of the peak intensities of the violet light V, the green light G, and the red light R. Accordingly, in the normal mode or the region-of-interest detection mode, the light source device 14 emits, as normal light, multicolor light for the normal mode or the region-of-interest detection mode including the violet light V, the blue light Bx, the green light G, and the red light R. The normal light has a certain intensity or more in the blue range to the red range and is thus substantially white.

Figure 5:
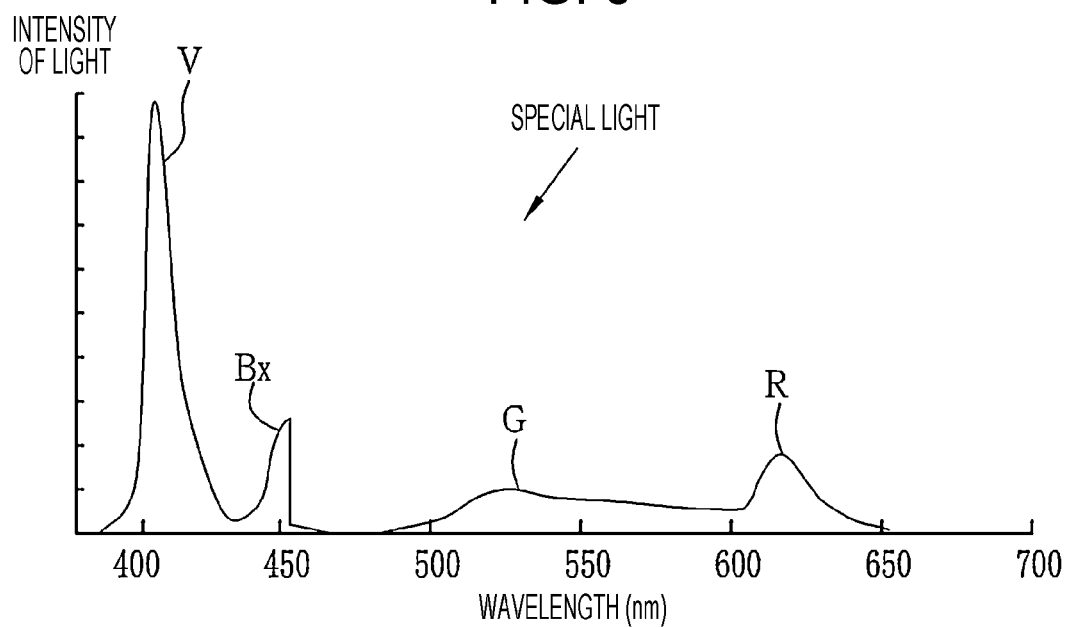
FIG. 5 is a graph illustrating a spectrum of special light according to the first embodiment.

In the special mode, the light source control unit 22 turns on all of the V-LED 20a, the B-LED 20b, the G-LED 20c, and the R-LED 20d. At this time, as illustrated in FIG. 5, the light amount ratio Ls among the violet light V, the blue light Bx, the green light G, and the red light R is set such that the peak intensity of the violet light V is higher than each of the peak intensities of the blue light Bx, the green light G, and the red light R and such that each of the peak intensities of the green light G and the red light R is lower than each of the peak intensities of the violet light V and the blue light Bx. Accordingly, in the special mode, the light source device 14 emits, as special light, multicolor light for the special mode including the violet light V, the blue light Bx, the green light G, and the red light R. The special light has a large proportion of the violet light V and is thus bluish. The special light does not necessarily need to include light of all the four colors, and may include light from at least one of the LEDs 20a to 20d of four colors. Preferably, the special light may have a main wavelength range, for example, a peak wavelength or a center wavelength, in a range that is 450 nm or less.

As illustrated in FIG. 2, the illumination light emitted by the light source unit 20 passes through a light path coupling unit (not illustrated) formed of a mirror, a lens, and the like and then enters a light guide 24 that extends through the insertion section 12a. The light guide 24 is built in the endoscope 12 and a universal cord, and causes the illumination light to propagate to the distal end portion 12d of the endoscope 12. The universal cord is a cord that connects the endoscope 12 to the light source device 14 and the processor device 16. A multimode fiber may be used as the light guide 24. As an example, a small-diameter fiber cable with a core diameter of 105 μm, a clad diameter of 125 μm, and a diameter including a protective layer serving as an outer cover of ϕ0.3 mm to ϕ0.5 mm may be used as the light guide 24.

The distal end portion 12d of the endoscope 12 is provided with an illumination optical system 30a and an imaging optical system 30b. The illumination optical system 30a has an illumination lens 32. An observation target is illuminated, via the illumination lens 32, with illumination light that has propagated through the light guide 24. The imaging optical system 30b has an objective lens 34, a magnifying optical system 36, and an image sensor 38 (corresponding to the "imaging device" of the present invention). Various types of light, such as reflected light, scattered light, and fluorescence from the observation target, enters the image sensor 38 through the objective lens 34 and the magnifying optical system 36. Accordingly, an image of the observation target is formed on the image sensor 38.

The magnifying optical system 36 includes a zoom lens 36a that magnifies an observation target, and a lens driving unit 36b that moves the zoom lens 36a in optical-axis directions CL. The zoom lens 36a is freely moved between a telephoto end and a wide end in accordance with zoom control by the lens driving unit 36b, thereby magnifying or demagnifying the image of the observation target formed on the image sensor 38.

The image sensor 38 is a color image sensor that performs imaging of an observation target irradiated with illumination light. Each of the pixels of the image sensor 38 is provided with a red (R) color filter, a green (G) color filter, or a blue (B) color filter. The image sensor 38 receives violet to blue light by using B pixels provided with the B color filter, receives green light by using G pixels provided with the G color filter, and receives red light by using R pixels provided with the R color filter. The image sensor 38 outputs image signals of individual colors of RGB from the pixels of the individual colors. The image sensor 38 transmits the output image signals to a correlated double sampling (CDS) circuit 40.

In the normal mode or the region-of-interest detection mode, the image sensor 38 performs imaging of an observation target illuminated with normal light, thereby outputting Bc image signals from the B pixels, outputting Gc image signals from the G pixels, and outputting Rc image signals from the R pixels. In the special mode, the image sensor 38 performs imaging of an observation target illuminated with special light, thereby outputting Bs image signals from the B pixels, outputting Gs image signals from the G pixels, and outputting Rs image signals from the R pixels.

A charge coupled device (CCD) image sensor, a complementary metal-oxide semiconductor (CMOS) image sensor, or the like can be used as the image sensor 38. Instead of the image sensor 38 provided with color filters of the primary colors RGB, a complementary-color image sensor including complementary-color filters of cyan (C), magenta (M), yellow (Y), and green (G) may be used. In the case of using the complementary-color image sensor, image signals of four colors CMYG are output. Thus, as a result of converting image signals of four colors CMYG into image signals of three colors RGB by using complementary color to primary color conversion, image signals of individual colors RGB similar to those in the image sensor 38 can be acquired. Alternatively, a monochrome sensor not provided with color filters may be used instead of the image sensor 38.

The CDS circuit 40 performs correlated double sampling (CDS) on analog image signals received from the image sensor 38. The image signals output from the CDS circuit 40 are input to an automatic gain control (AGC) circuit 42. The AGC circuit 42 performs automatic gain control (AGC) on the image signals input thereto. An analog to digital (A/D) conversion circuit 44 converts the analog image signals output from the AGC circuit 42 into digital image signals. The A/D conversion circuit 44 inputs the digital image signals generated through the A/D conversion to the processor device 16.

As illustrated in FIG. 2, the processor device 16 includes an image signal acquiring unit 50 (corresponding to the "medical image acquiring unit" of the present invention), a digital signal processor (DSP) 52, a noise reducing unit 54, an image processing unit 56, and a display control unit 58.

The image signal acquiring unit 50 acquires digital image signals corresponding to an observation mode from the endoscope 12. In the normal mode or the region-of-interest detection mode, the image signal acquiring unit 50 acquires Bc image signals, Gc image signals, and Rc image signals. In the special mode, the image signal acquiring unit 50 acquires Bs image signals, Gs image signals, and Rs image signals. In the region-of-interest detection mode, the image signal acquiring unit 50 acquires Bc image signals, Gc image signals, and Rc image signals of one frame during illumination with normal light, and acquires Bs image signals, Gs image signals, and Rs image signals of one frame during illumination with special light.

The DSP 52 performs various signal processing operations, such as defect correction processing, offset processing, DSP gain correction processing, linear matrix processing, gamma conversion processing, and demosaicing processing, on the image signals acquired by the image signal acquiring unit 50. The defect correction processing corrects a signal of a defective pixel of the image sensor 38. The offset processing removes a dark current component from the image signal that has been subjected to the defect correction processing and sets an accurate zero level. The DSP gain correction processing multiplies the image signal that has been subjected to the offset processing by a specific DSP gain, thereby adjusting the signal level.

The linear matrix processing increases the color reproducibility of the image signal that has been subjected to the DSP gain correction processing. The gamma conversion processing adjusts the brightness and chroma of the image signal that has been subjected to the linear matrix processing. The image signal that has been subjected to the gamma conversion processing is subjected to demosaicing processing (also referred to as isotropic processing or synchronization processing), thereby generating, through interpolation, a signal of a color insufficient in each pixel. The demosaicing processing enables all pixels to have signals of individual colors RGB. The noise reducing unit 54 performs noise reduction processing using, for example, a moving-average method, a median filter method, or the like, on the image signal that has been subjected to the demosaicing processing and so forth in the DSP 52, thereby reducing noise. The image signal that has been subjected to the noise reduction is input to the image processing unit 56.

The image processing unit 56 includes a normal-mode image processing unit 60, a special-mode image processing unit 62, and a region-of-interest-detection-mode image processing unit 64. The normal-mode image processing unit 60 operates when the normal mode is set, and performs color conversion processing, color enhancement processing, and structure enhancement processing on the Bc image signals, Gc image signals, and Rc image signals that have been received. In the color conversion processing, color conversion processing is performed on the RGB image signals by using 3×3 matrix processing, gradation transformation processing, three-dimensional look up table (LUT) processing, and the like.

The color enhancement processing is performed on the RGB image signals that have been subjected to color conversion processing. The structure enhancement processing is processing of enhancing the structure of an observation target and is performed on the RGB image signals that have been subjected to the color enhancement processing. The above-described various image processing operations enable a normal image to be acquired. The normal image is an image acquired on the basis of normal light including the violet light V, the blue light Bx, the green light G, and the red light R with a well-balanced ratio, and is thus an image with natural colors. The normal image is input to the display control unit 58.

The special-mode image processing unit 62 operates when the special mode is set. The special-mode image processing unit 62 performs color conversion processing, color enhancement processing, and structure enhancement processing on the Bs image signals, Gs image signals, and Rs image signals that have been received. The processing performed in the color conversion processing, the color enhancement processing, and the structure enhancement processing is similar to that performed by the normal-mode image processing unit 60. The above-described various image processing operations enable a special image to be acquired. The special image is an image acquired on the basis of special light in which the amount of the violet light V having a high hemoglobin absorption coefficient of blood vessels is larger than the amount of the blue light Bx, the green light G, and the red light R, and thus the resolution of a blood vessel structure and a gland duct structure is higher than that of other structures. The special image is input to the display control unit 58.

Figure 6:
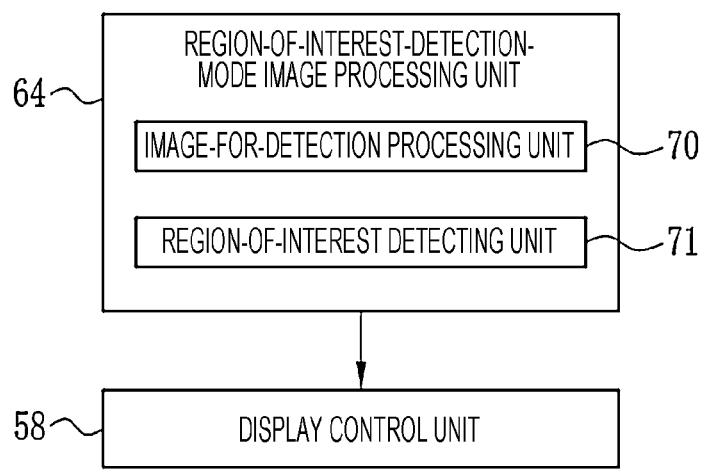
FIG. 6 is a block diagram illustrating functions of a region-of-interest-detection-mode image processing unit and a display control unit.

The region-of-interest-detection-mode image processing unit 64 operates when the region-of-interest detection mode is set. As illustrated in FIG. 6, the region-of-interest-detection-mode image processing unit 64 has an image-for-detection processing unit 70 and a region-of-interest detecting unit 71. The image-for-detection processing unit 70 performs image processing similar to that performed by the normal-mode image processing unit 60, such as color conversion processing, on the Bc image signals, Gc image signals, and Rc image signals that have been received, thereby sequentially acquiring endoscopic images.

The region-of-interest detecting unit 71 analyzes an endoscopic image and performs region-of-interest detection processing for detecting a region of interest in an observation target. In this embodiment, the region-of-interest detecting unit 71 detects, as a region of interest, a lesion portion (for example, a tumor, an inflammation, or the like) in the observation target. In this case, the region-of-interest detecting unit 71 first divides the endoscopic image into a plurality of small regions, for example, square regions each formed of a certain number of pixels. Subsequently, the region-of-interest detecting unit 71 calculates image feature quantities from the divided endoscopic image. Subsequently, the region-of-interest detecting unit 71 recognizes, on the basis of the calculated feature quantities, whether or not each of the small regions is a lesion portion. Preferably, such recognition processing may be a machine learning algorithm such as a convolutional neural network or deep learning.

Preferably, a feature quantity calculated from an endoscopic image by the region-of-interest detecting unit 71 may be the shape or color of a predetermined portion in an observation target, or an index value acquired from the shape or color. Preferably, for example, the feature quantity may be at least any one of the density of a blood vessel, the shape of a blood vessel, the number of branches of a blood vessel, the thickness of a blood vessel, the length of a blood vessel, the degree of meandering of a blood vessel, the depth of a blood vessel, the shape of a gland duct, the shape of an opening portion of a gland duct, the length of a gland duct, the degree of meandering of a gland duct, or color information, or the value of a combination of two or more of them.

Finally, the region-of-interest detecting unit 71 extracts a group of small regions specified as the same type as one lesion portion. The region-of-interest detecting unit 71 associates information indicating the position, size, type, and the like of the extracted lesion portion as a detection result with the endoscopic image. The region-of-interest-detection-mode image processing unit 64 outputs the endoscopic image associated with the detection result to the display control unit 58.

The display control unit 58 performs display control for displaying an image or data from the image processing unit 56 on the monitor 18. When the normal mode is set, the display control unit 58 performs control to display a normal image on the monitor 18. When the special mode is set, the display control unit 58 performs control to display a special image on the monitor 18.

When the region-of-interest detection mode is set, the display control unit 58 displays the region of interest detected from the endoscopic image by the region-of-interest detecting unit 71 in a manner of emphasized display. In the case of displaying the region of interest in a manner of emphasized display, the display control unit 58 first sets an emphasized region for emphasizing the region of interest on the basis of the endoscopic image output from the region-of-interest-detection-mode image processing unit 64 and the detection result associated with the endoscopic image.

Figure 7:
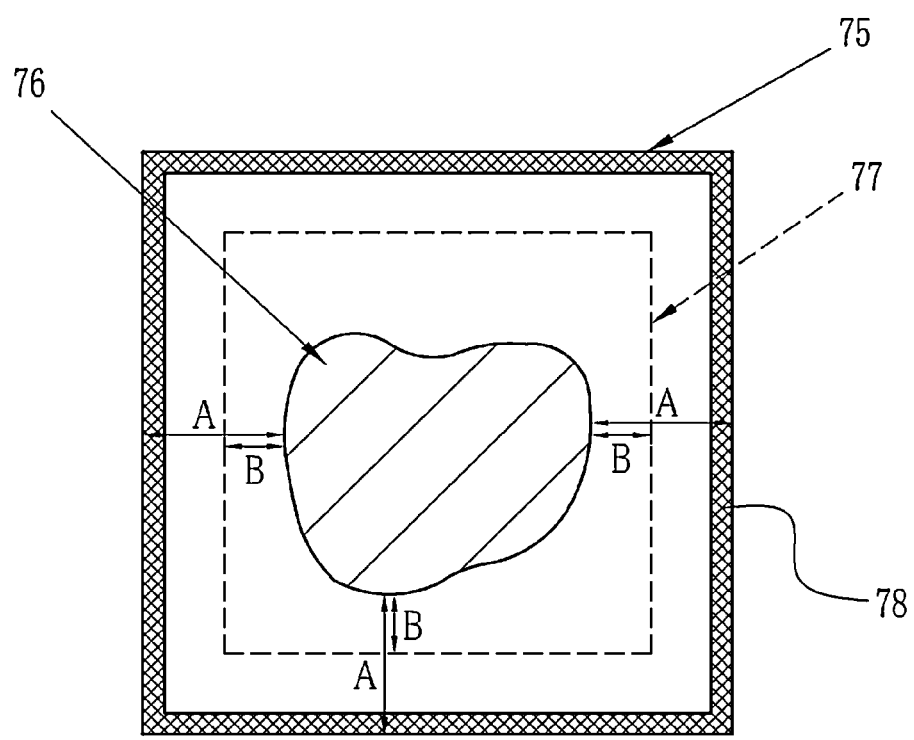
FIG. 7 is an explanatory diagram illustrating an emphasized region and a reference region that are set in a case where the display control unit performs emphasized display of a region of interest.

As illustrated in FIG. 7, the display control unit 58 sets an emphasized region having a larger area than a lesion portion 76 as a region of interest and including the lesion portion 76. In this embodiment, a square region is set as an emphasized region 75. The emphasized region 75 has, for example, a square outer periphery that is set with a predetermined distance A or more from the outer periphery of the lesion portion 76.

When or after setting the emphasized region 75, the display control unit 58 sets a reference region 77 on an outer side of the lesion portion 76 and an inner side of the emphasized region 75. In this embodiment, a square region having a smaller area than the emphasized region 75 and including the lesion portion 76 is set as the reference region 77. The reference region 77 has, for example, a square outer periphery that is set with a predetermined distance B or more (the distance B is smaller than the distance A) from the outer periphery of the lesion portion 76.

The display control unit 58 performs emphasized display on the emphasized region 75 that has been set in the above-described manner. That is, the display control unit 58 superimposes a figure for emphasized display on the position of the emphasized region 75 in the endoscopic image. In this embodiment, the display control unit 58 displays a figure 78 that surrounds the lesion portion 76 and that is square frame shaped (frame shaped) at the position of the emphasized region 75. Although the reference region 77 is illustrated with a broken line for convenience of description, the broken line indicating the reference region 77 is not necessarily displayed in an actual endoscopic image.

The figure 78 for emphasized display is displayed in a manner different from that of the other portion of the endoscopic image. For example, the display control unit 58 extracts a color contained in high proportion in the endoscopic image and displays the figure 78 in a color having a hue different from that of the extracted color.

After setting the emphasized region 75 and the reference region 77, the display control unit 58 determines whether or not to change the setting of the emphasized region 75 in accordance with the amount of variation in the lesion portion 76 in the endoscopic image. Specifically, in a case where at least a part of the lesion portion 76 has shifted to the outside of the reference region 77, the display control unit 58 resets the emphasized region 75 and the reference region 77.

Figure 8:
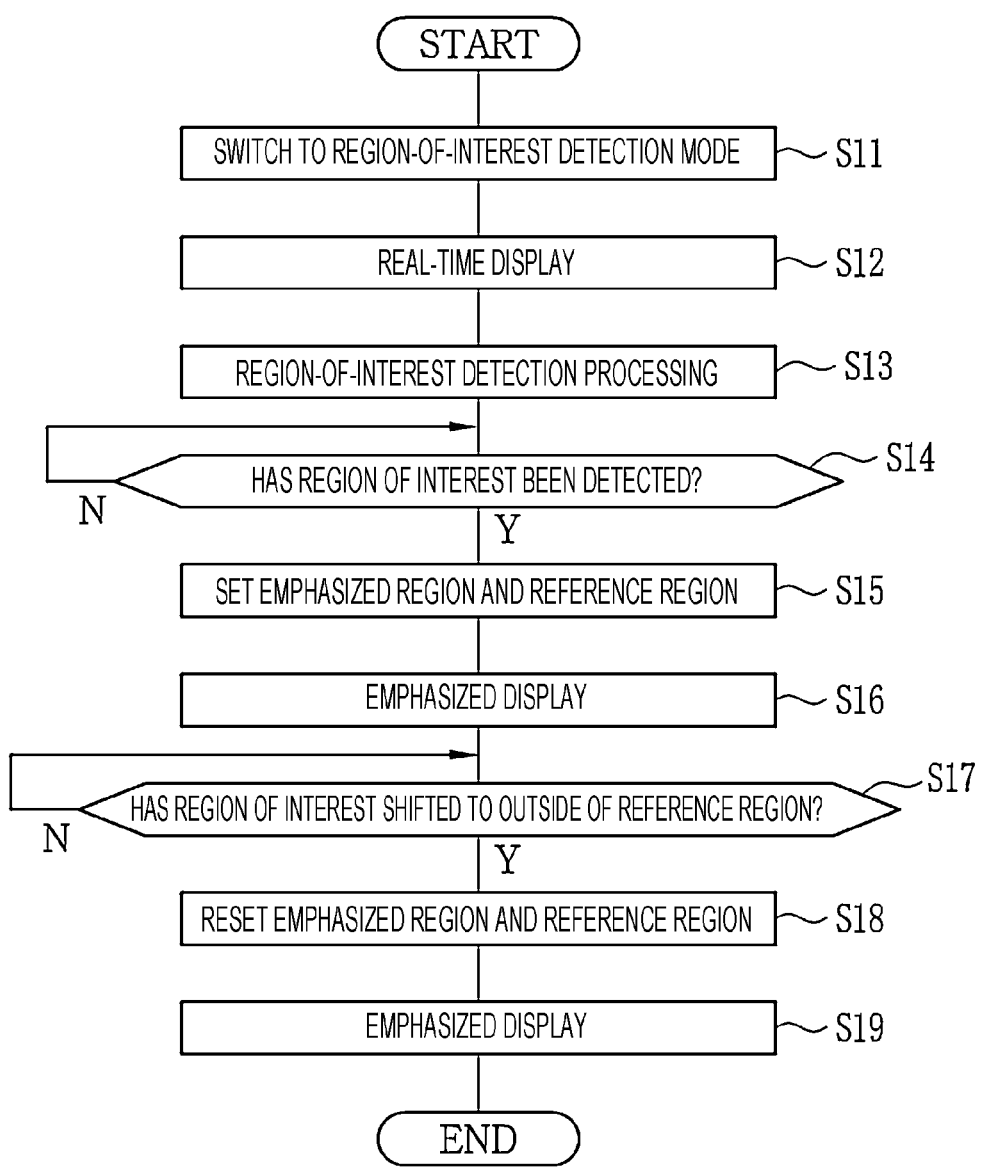
FIG. 8 is a flowchart illustrating a process of a region-of-interest detection mode.

Hereinafter, a process of resetting the emphasized region 75 and the reference region 77 by the display control unit 58 in the region-of-interest detection mode will be described with reference to the flowchart illustrated in FIG. 8 and the explanatory diagram illustrated in FIG. 9. A medical doctor who is a user operates the mode switching unit 13c to switch the mode to the region-of-interest detection mode (S11). Accordingly, an observation target is illuminated with illumination light for the region-of-interest detection mode. The image sensor 38 performs imaging of the observation target illuminated with the illumination light for the region-of-interest detection mode, and thereby an endoscopic image is acquired. In the region-of-interest detection mode, the display control unit 58 sequentially acquires endoscopic images and displays the endoscopic images on a display screen 81 of the monitor 18 in real time (S12).

During real-time display in the region-of-interest detection mode, the region-of-interest detecting unit 71 performs region-of-interest detection processing for detecting a region of interest in the observation target on the acquired endoscopic image (S13). In a case where a region of interest has been detected (Y in S14), the detection result of the region-of-interest detecting unit 71 is output in association with the endoscopic image.

Figure 9:
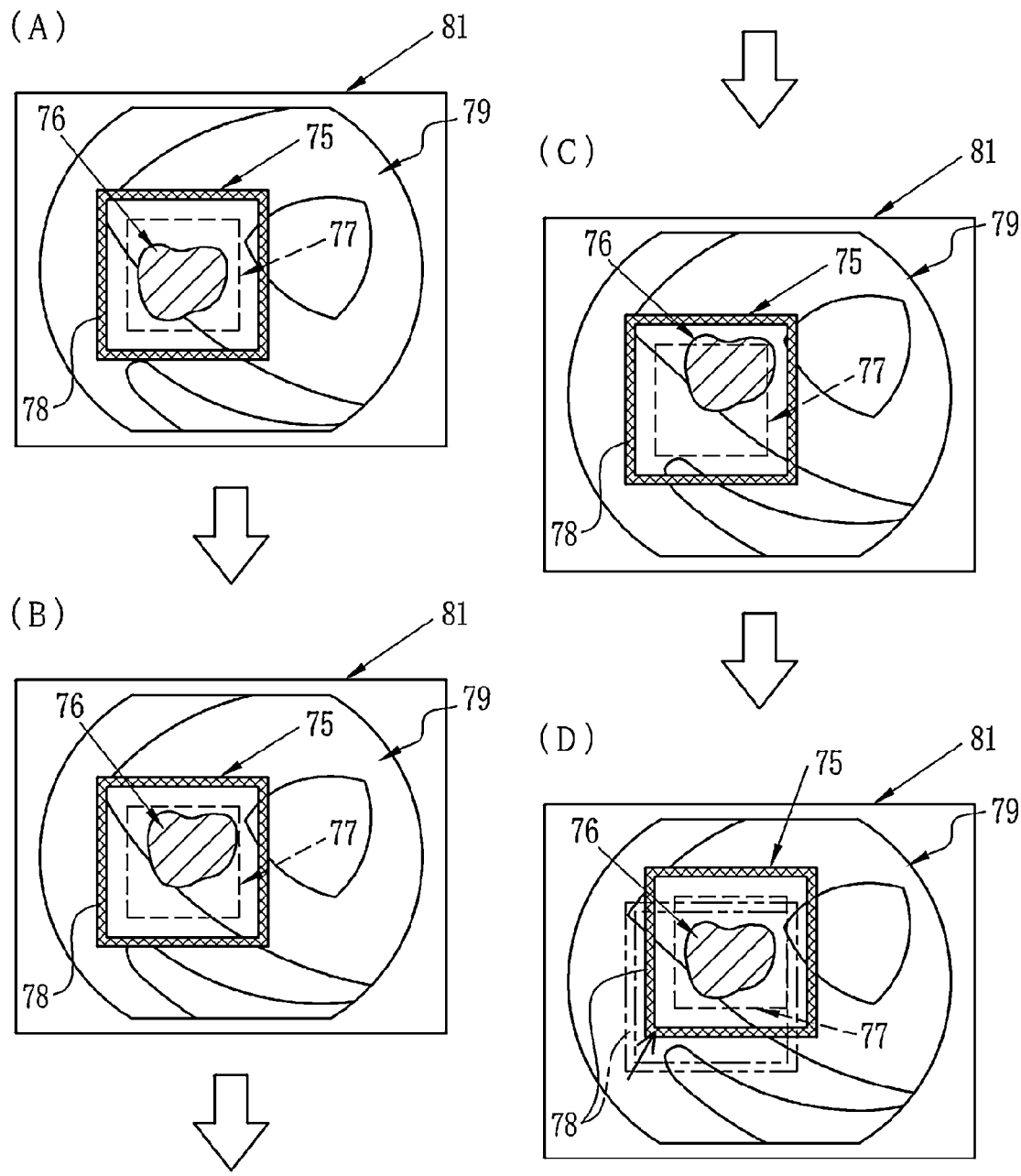
FIG. 9 is an explanatory diagram illustrating an example of a display screen in a case where the display control unit performs emphasized display of a region of interest and illustrating changes in the display screen in chronological order.

In a case where the lesion portion 76 as a region of interest is detected in the observation target as illustrated in part (A) of FIG. 9, that is, in a case where the detection result is associated with an endoscopic image 79, the display control unit 58 sets the emphasized region 75 and the reference region 77 by using the detection result associated with the endoscopic image 79, in particular, information indicating the position and size of the lesion portion 76 (S15).

After setting the emphasized region 75 and the reference region 77, the display control unit 58 superimposes the figure 78 for emphasized display on the position of the emphasized region 75 in the endoscopic image 79 (S16). In FIG. 9 to FIG. 11 and FIG. 14, the difference in color between the figure 78 and the other portion of the endoscopic image 79 is expressed by the presence or absence of hatching, for convenience of illustration. On the other hand, in a case where the lesion portion 76 is not detected in the observation target (N in S14), emphasized display is not performed as a matter of course.

Subsequently, the display control unit 58 causes the figure 78 to be displayed for emphasized display (S16) and monitors whether or not the lesion portion 76 shifts to the outside of the reference region 77. In a case where at least a part of the lesion portion 76 has shifted to the outside of the reference region 77 (Y in S17), the display control unit 58 resets the emphasized region 75 and the reference region 77 (S18). In the example illustrated in FIG. 9, the position of the lesion portion 76 in the endoscopic image 79 moves from the inside of the reference region 77 (the state illustrated in part (B) of FIG. 9) to the outside of the reference region 77 (the state illustrated in part (C) of FIG. 9), and thus the positions of the emphasized region 75 and the reference region 77 that are reset by using information indicating the position and size of the lesion portion 76 are moved as a matter of course.

The display control unit 58 superimposes the figure 78 for emphasized display on the position of the emphasized region 75 that has been reset (S19). Accordingly, as illustrated in part (D) of FIG. 9, the figure 78 moves from the before-reset position indicated by two-dot chain lines to the after-reset position indicated by solid lines. On the other hand, in a case where the lesion portion 76 does not shift to the outside of the reference region 77 (N in S17), the display control unit 58 resets neither the emphasized region 75 nor the reference region 77, and thus the figure 78 for emphasized display is kept in the same state.

As described above, the lesion portion 76 in the endoscopic image 79 is displayed in a manner of emphasized display by using the figure 78, and thus the medical doctor is able to easily recognize the exact position of the lesion portion 76. In a case where the lesion portion 76 detected from the endoscopic image 79 shifts within the reference region 77, the figure 78 for emphasized display is kept in the same state. Only in a case where at least a part of the lesion portion 76 has shifted to the outside of the reference region 77, the figure 78 is moved. Thus, the time period during which the figure 78 changes is short, and the amount of flicker in the display screen 81 is small. Thus, the medical doctor is able to concentrate on observing the lesion portion 76 without being hindered by display of the figure 78.

Second Embodiment

Figure 10:
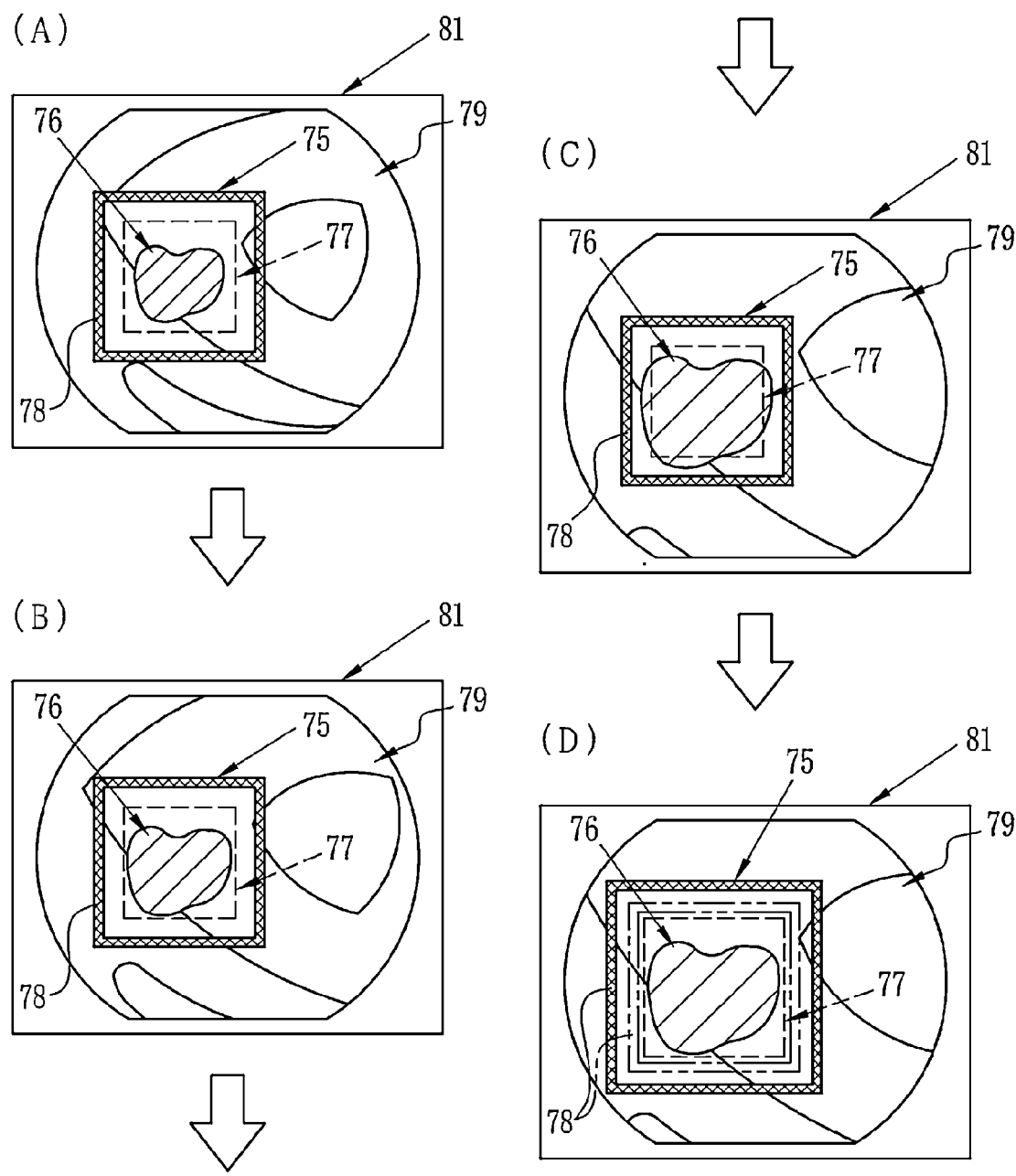
FIG. 10 is an explanatory diagram illustrating changes in the display screen in chronological order according to a second embodiment.

In the above-described first embodiment, an example is given in which the lesion portion 76 detected from the endoscopic image 79 shifts with the size thereof unchanged (the example illustrated in FIG. 9), and thus the figure 78 for emphasized display is changed only in the position in accordance with the shift of the lesion portion 76. Alternatively, the size of the figure 78 may be changed in accordance with the shift of the lesion portion 76. FIG. 10 illustrates an example of a case where the lesion portion 76 detected from the endoscopic image 79 is enlarged by, for example, changing the zoom magnification of the endoscope 12.

As illustrated in part (A) of FIG. 10, in a case where the lesion portion 76 as a region of interest is detected in an observation target under the region-of-interest detection mode, the display control unit 58 sets the emphasized region 75 and the reference region 77 and superimposes the figure 78 for emphasized display, as in the above-described first embodiment.

Subsequently, the lesion portion 76 in the endoscopic image 79 shifts, and the lesion portion 76 is enlarged from the inside of the reference region 77 (the state illustrated in part (B) of FIG. 10) to the outside of the reference region 77 (the state illustrated in part (C) of FIG. 10). In a case where at least a part of the lesion portion 76 has shifted to the outside of the reference region 77, the display control unit 58 resets the emphasized region 75 and the reference region 77. In the example illustrated in FIG. 10, the lesion portion 76 is enlarged, and thus the sizes of the emphasized region 75 and the reference region 77 that are reset by using information indicating the position and size of the lesion portion 76 are increased as a matter of course.

The display control unit 58 superimposes the figure 78 for emphasized display on the position of the emphasized region 75 that has been reset. Accordingly, as illustrated in part (D) of FIG. 10, the figure 78 is enlarged from the size of the before-reset emphasized region 75 indicated by two-dot chain lines to the size of the after-reset emphasized region 75 indicated by solid lines.

As described above, in a case where the lesion portion 76 detected from the endoscopic image 79 is enlarged within the reference region 77, the figure 78 for emphasized display is kept in the same state. Only in a case where at least a part of the lesion portion 76 has shifted to the outside of the reference region 77, the figure 78 is enlarged. Accordingly, the time period during which the figure 78 changes is short, and the amount of flicker in the display screen 81 is small.

Third Embodiment

In the above-described second embodiment, in a case where the lesion portion 76 detected from the endoscopic image 79 is significantly enlarged, the figure 78 for emphasized display is also enlarged in accordance with the lesion portion 76, and thus the amount of flicker based on the change is large. Thus, in the third embodiment described below, the display control unit 58 sets in advance two threshold values, a first threshold value $\alpha 1$ and a second threshold value $\alpha 2$ greater than the first threshold value $\alpha 1$. In a case where the enlargement ratio of the area of the lesion portion 76 exceeds the first threshold value $\alpha 1$, the figure 78 for emphasized display is also enlarged in accordance with the lesion portion 76 as in the above-described second embodiment. In a case where the enlargement ratio of the area of the lesion portion 76 exceeds the second threshold value $\alpha 2$, emphasized display is changed to an icon or the like having a small display area.

Figure 11:
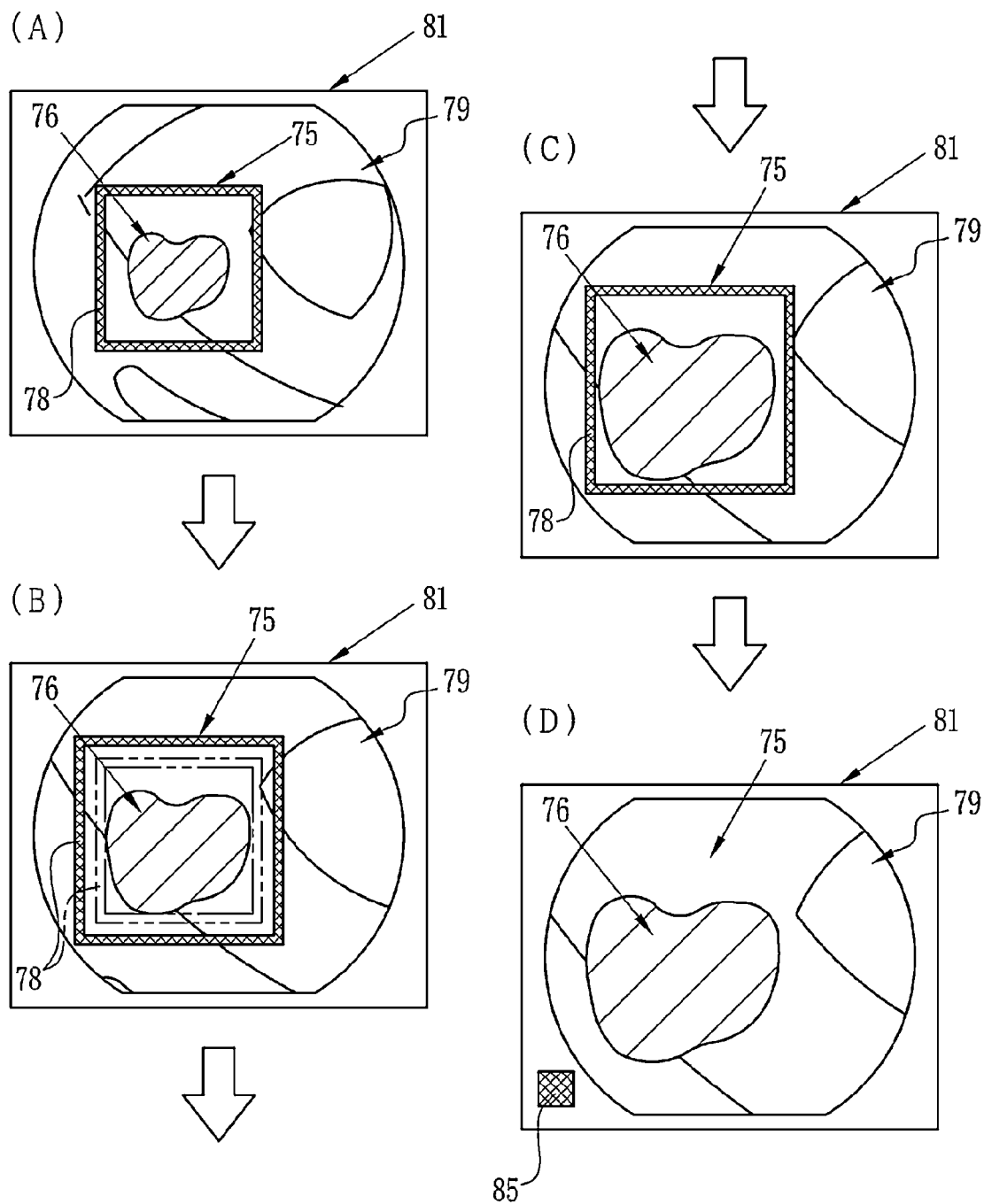
FIG. 11 is an explanatory diagram illustrating changes in the display screen in chronological order according to a third embodiment.

First, as illustrated in part (A) of FIG. 11, in a case where the lesion portion 76 as a region of interest is detected in an observation target under the region-of-interest detection mode, the display control unit 58 sets the emphasized region 75 and superimposes the FIG. 78 for emphasized display as in the above-described first embodiment.

After setting the emphasized region 75, the display control unit 58 monitors an enlargement ratio E of the area of the lesion portion 76. Specifically, the display control unit 58 compares the enlargement ratio E with the first threshold value $\alpha 1$ and the second threshold value $\alpha 2$ set in advance. The enlargement ratio E is the ratio of the area of the currently displayed lesion portion 76 to the area of the lesion portion 76 when lesion portion 76 is detected for the first time after the start of acquisition of the endoscopic image 79 (that is, when the emphasized region 75 is set).

In a case where the lesion portion 76 is enlarged in the endoscopic image 79 and the enlargement ratio E exceeds the first threshold value $\alpha 1$, the display control unit 58 resets the emphasized region 75. In the resetting in a case where the enlargement ratio E exceeds the first threshold value $\alpha 1$, the size of the emphasized region 75 is reset as in the above-described second embodiment. The display control unit 58 superimposes the figure 78 for emphasized display on the position of the emphasized region 75 that has been reset (hereinafter, this is referred to as first-stage emphasized display for convenience of description). Accordingly, as illustrated in part (B) of FIG. 11, the figure 78 is enlarged from the before-reset size indicated with two-dot chain lines to the after-reset size indicated with solid lines.

In the first-stage emphasized display, as in the above-described second embodiment, the emphasized region 75 and the reference region 77 may be set, and in a case where at least a part of the lesion portion 76 has shifted to the outside of the reference region 77, the display control unit 58 may reset the emphasized region 75 and the reference region 77.

After that, in a case where the lesion portion 76 is further enlarged within the endoscopic image 79 and the enlargement ratio E exceeds the second threshold value $\alpha 2$ (the state illustrated in part (C) of FIG. 11), the display control unit 58 does not reset the emphasized region 75 but changes the emphasized display (hereinafter this is referred to as second-stage emphasized display for convenience of description). In this embodiment, in the case of the second-stage emphasized display, the frame-shaped figure 78 is not displayed unlike in the first-stage emphasized display, but an icon 85 is superimposed outside the part to be observed of the endoscopic image 79 and near the lesion portion 76. In this embodiment, the icon 85 for emphasized display is a square figure. Alternatively, the icon 85 may be another figure. The area of the icon 85 is smaller than the area of the figure 78 before change of emphasized display.

As described above, in a case where the lesion portion 76 detected from the endoscopic image 79 is significantly enlarged, the figure 78 is kept in the same state until the enlargement ratio E exceeds the first threshold value $\alpha 1$, and the figure 78 is enlarged from when the enlargement ratio E exceeds the first threshold value $\alpha 1$ to when the enlargement ratio E exceeds the second threshold value $\alpha 2$. After the enlargement ratio E exceeds the second threshold value $\alpha 2$, the emphasized display is changed and the icon 85 having an area smaller than the area of the figure 78 is displayed. Thus, the change in the display screen 81 is small and the amount of flicker is small. In this embodiment, the square-frame-shaped FIG. 78 is changed to the square-shaped icon 85, and thus the emphasized display is easily recognized.

Figure 12:
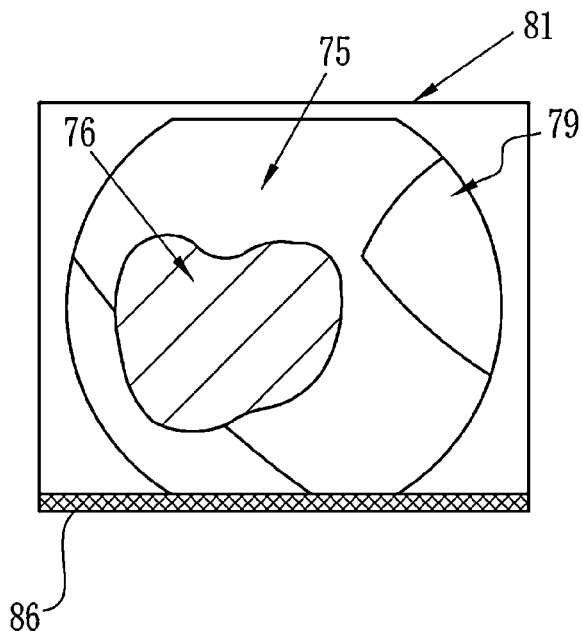
FIG. 12 is an explanatory diagram illustrating a first modification example of the third embodiment.
Figure 13:
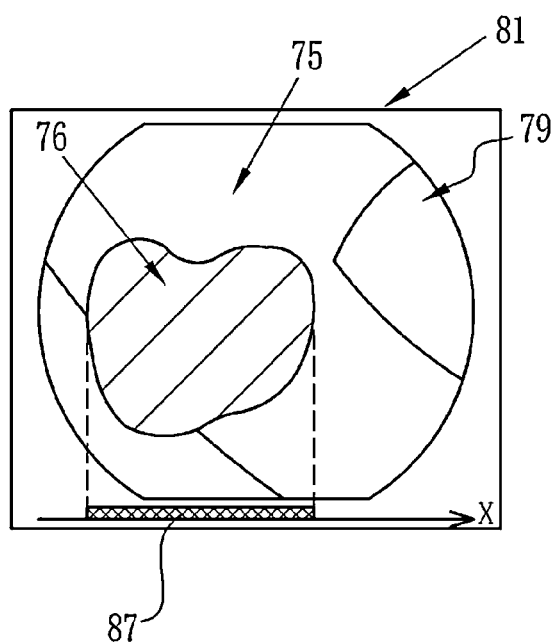
FIG. 13 is an explanatory diagram illustrating a second modification example of the third embodiment.

In the case of the second-stage emphasized display, the icon to be displayed is not limited to the icon 85 illustrated in FIG. 11, and any icon with an area smaller than the area of the figure 78 before change of the emphasized display may be used. For example, as illustrated in FIG. 12, in the case of the second-stage emphasized display, a band-shaped FIG. 86 may be displayed along the endoscopic image 79 and the display screen 81. Alternatively, as illustrated in FIG. 13, a coordinate axis X may be set along the endoscopic image 79, and a display manner may be changed only in a portion 87 corresponding to the lesion portion 76 on the coordinate axis X. In the example illustrated in FIG. 13, the band-shaped portion 87 corresponding to the lesion portion 76 along the coordinate axis X has a large width and is hatched. Alternatively, any display manner representing a difference may be used, for example, the color or luminance of the portion corresponding to the lesion portion 76 may be changed along the coordinate axis X.

Fourth Embodiment

In each of the above-described embodiments, an emphasized region and a reference region are set by using information of a region of interest detected from an endoscopic image or the like, and whether or not to change the setting of the emphasized region is determined. Alternatively, representative coordinates of a lesion portion may be set without a reference region being set, and whether or not to change the setting of an emphasized region may be determined in a case where the position of the representative coordinates has moved beyond a threshold value. In the fourth embodiment described below, the display control unit 58 sets representative coordinates 91 of the lesion portion 76, and resets the position of the emphasized region 75 in a case where the position of the representative coordinates 91 has moved beyond a threshold value.

Figure 14:
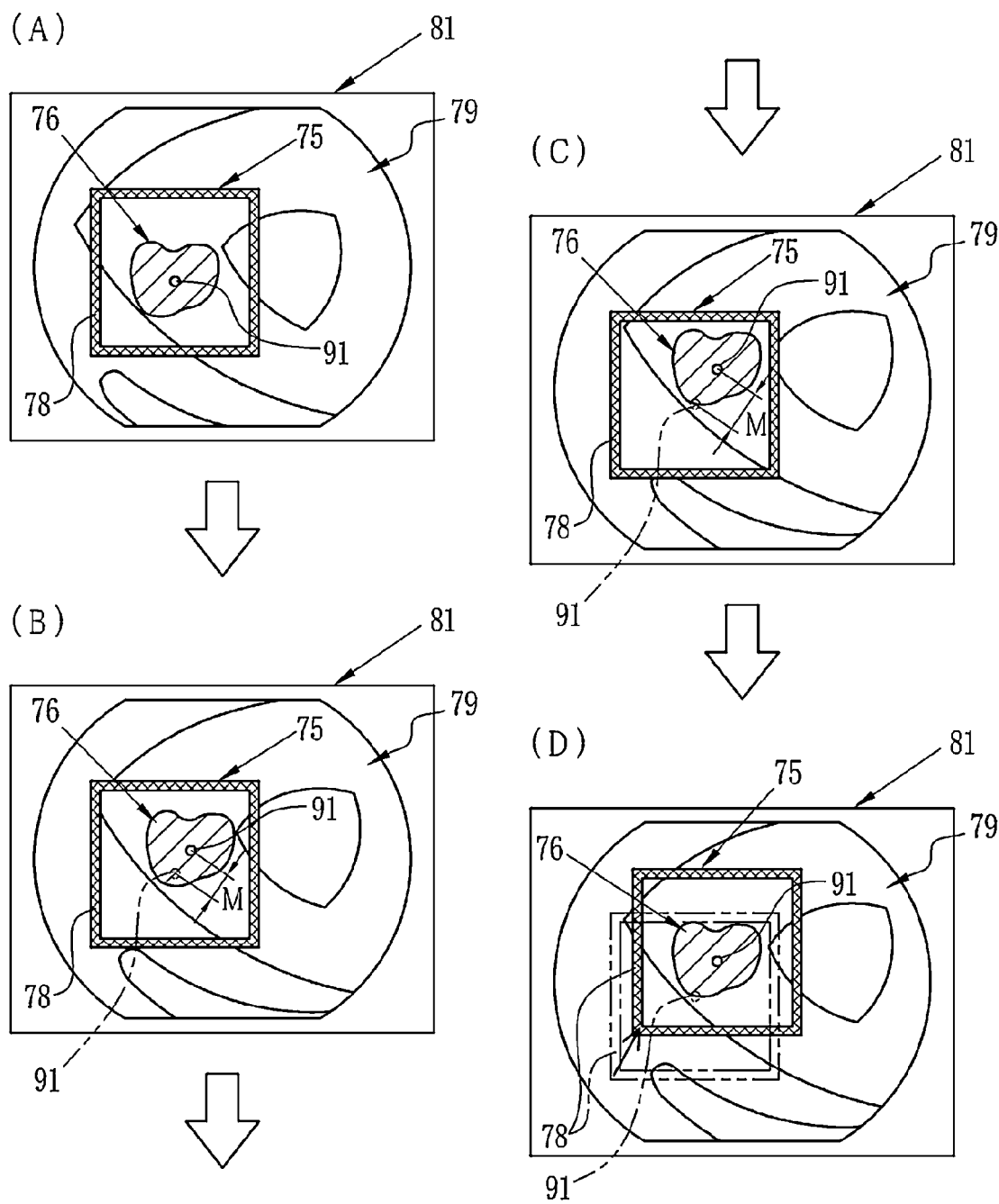
FIG. 14 is an explanatory diagram illustrating changes in the display screen in chronological order according to a fourth embodiment.

First, as illustrated in part (A) of FIG. 14, in a case where the lesion portion 76 as a region of interest is detected in an observation target under the region-of-interest detection mode, the display control unit 58 sets the emphasized region 75 as in the above-described first embodiment, and determines the representative coordinates 91. The display control unit 58 uses, for example, the coordinates of the position of the center of gravity of the lesion portion 76 as the representative coordinates 91. In this embodiment, the center of the area of the lesion portion 76 is calculated as the position of the center of gravity.

After setting the emphasized region 75 and the representative coordinates 91, the display control unit 58 superimposes the figure 78 for emphasized display on the position of the emphasized region 75 within the endoscopic image 79. In FIG. 14, a circular figure is displayed at the position of the representative coordinates 91. Alternatively, the figure is not necessarily displayed at the position of the representative coordinates 91.

After setting the emphasized region 75, the display control unit 58 monitors the amount of movement of the representative coordinates 91. Specifically, the amount of movement is the amount of movement from an initial position of the representative coordinates 91 when the lesion portion 76 is detected for the first time after the start of acquisition of the endoscopic image 79 (that is, when the emphasized region 75 is set) to the position of the representative coordinates 91 in the currently displayed lesion portion 76.

Subsequently, as illustrated in parts (B) and (C) of FIG. 14, the lesion portion 76 shifts within the endoscopic image 79, and the representative coordinates 91 move together with the lesion portion 76. A reference symbol M represents the amount of movement of the representative coordinates 91. In a case where the amount of movement M of the representative coordinates 91 exceeds a threshold value $\beta$, the display control unit 58 resets the emphasized region 75. In the example illustrated in FIG. 14, the representative coordinates 91 of the lesion portion 76 are moved, and thus the position of the emphasized region 75 that is reset using information indicating the position and size of the lesion portion 76 is moved as a matter of course.

The display control unit 58 superimposes the figure 78 for emphasized display on the position of the emphasized region 75 that has been reset. As illustrated in part (D) of FIG. 14, the figure 78 is moved from the before-reset position indicated by two-dot chain lines to the after-reset position indicated by solid lines. On the other hand, in a case where the amount of movement M of the representative coordinates 91 does not exceed the threshold value $\beta$, the display control unit 58 does not reset the emphasized region 75, and thus the figure 78 for emphasized display is kept in the same state.

As described above, in a case where the lesion portion 76 detected from the endoscopic image 79 shifts and the amount of movement M of the representative coordinates 91 does not exceed the threshold value, the figure 78 for emphasized display is kept in the same state. The figure 78 is moved only in a case where the amount of movement M of the representative coordinates 91 exceeds the threshold value. Thus, the amount of change in the figure 78 is small, and the amount of flicker in the display screen 81 is small.

In each of the above-described embodiments, the figure for emphasized display is square frame shaped except in the second-stage emphasized display in the third embodiment, but the frame shape is not limited thereto. Any frame shape other than a rectangle (square) capable of surrounding a region of interest, for example, polygon, circle, or ellipse, may be used.

In each of the above-described embodiments, the display control unit 58 superimposes a frame-shaped figure on the position of an emphasized region for emphasized display except in the second-stage emphasized display in the third embodiment, but the emphasized display is not limited thereto. For emphasized display, the color of an emphasized region may be changed. In this case, in a case where the lesion portion 76 as a region of interest is detected and an emphasized region is set, the display control unit 58 may change the color of the emphasized region for emphasized display to a color different from the original color, for example, may extract a color contained in high proportion in the endoscopic image and may change the color of the emphasized region to a color different from the color of the other portion of the endoscopic image. Here, a different color is, for example, a color having a different hue.

The emphasized display of the emphasized region is not limited to those described above. Any image processing may be applied as long as visual distinction from the surroundings can be achieved, such as chroma change processing, contrast processing, negative-positive reverse processing, or filtering processing. Alternatively, emphasized display using image processing of the emphasized region and emphasized display using a figure surrounding a lesion portion in each of the above-described embodiments may be combined.

Although an observation target is illuminated by using the four-color LEDs 20*a* to 20*d* in each of the above-described embodiments, the observation target may be illuminated by using a laser light source and a fluorescent body. Although an observation target is illuminated by using the four-color LEDs 20*a* to 20*d* in each of the above-described embodiments, the observation target may be illuminated by using a white light source such as a xenon lamp and a rotary filter. Imaging of an observation target may be performed by using a monochrome image sensor instead of the color image sensor 38.

In the above-described embodiments, the medical image processing apparatus of the present invention is applied to an endoscope system that acquires an endoscopic image as a medical image. Obviously, the medical image processing apparatus of the present invention can be applied to various types of endoscope systems, such as a capsule endoscope. Also, the medical image processing apparatus of the present invention can be applied to various types of medical image apparatuses that acquire other types of medical images, such as an X-ray image, a CT image, an MR image, an ultrasound image, a pathological image, and a positron emission tomography (PET) image.

In the above-described embodiments, the hardware structure of a processing unit that executes various processing operations, such as the image processing unit 56, may be various types of processors described below. The various types of processors include a central processing unit (CPU), which is a general-purpose processor executing software (program) and functioning as various processing units; a graphical processing unit (GPU); a programmable logic device (PLD), which is a processor whose circuit configuration is changeable after manufacturing, such as a field programmable gate array (FPGA); a dedicated electric circuit, which is a processor having a circuit configuration designed exclusively for executing various processing operations, and the like.

A single processing unit may be constituted by one of these various types of processors or may be constituted by a combination of two or more processors of the same type or different types (for example, a combination of a plurality of FPGAs, a combination of a CPU and an FPGA, or a combination of a CPU and a GPU). A plurality of processing units may be constituted by a single processor. Examples of constituting a plurality of processing units by a single processor are as follows. First, as represented by a computer of a client or server, a single processor is constituted by a combination of one or more CPUs and software, and the processor functions as a plurality of processing units. Secondly, as represented by a system on chip (SoC), a processor in which a single integrated circuit (IC) chip implements the function of an entire system including a plurality of processing units is used. In this way, various types of processing units are constituted by using one or more of the above-described various types of processors as a hardware structure.

Furthermore, the hardware structure of these various types of processors is, more specifically, electric circuitry including a combination of circuit elements, such as semiconductor elements.

REFERENCE SIGNS LIST 10 endoscope system
12 endoscope
12a insertion section
12b operation section
12c bending portion
12d distal end portion
13a angle knob
13b still image acquiring unit
13c mode switching unit
13d zoom operation unit
14 light source device
16 processor device
18 monitor
19 console
20 light source unit
20a V-LED
20b B-LED
20c G-LED
20d R-LED
22 light source control unit
23 wavelength cut filter
24 light guide
30a illumination optical system
30b imaging optical system
32 illumination lens
34 objective lens
36 magnifying optical system
36a zoom lens
36b lens driving unit
38 image sensor
40 CDS circuit
42 AGC circuit
44 A/D conversion circuit
50 image signal acquiring unit
52 DSP
54 noise reducing unit
56 image processing unit
58 display control unit
60 normal-mode image processing unit
62 special-mode image processing unit
64 region-of-interest-detection-mode image processing unit
70 image-for-detection processing unit
71 region-of-interest detecting unit
75 emphasized region
76 lesion portion
77 reference region
78 figure
79 endoscopic image
81 display screen
85 icon
86 figure
87 portion
91 representative coordinates

What is claimed is:

1. A medical image processing apparatus comprising:
a processor configured to function as:
a medical image acquiring unit that acquires a medical image through imaging of an observation target;
a region-of-interest detecting unit that detects a region of interest in the observation target from the medical image acquired by the medical image acquiring unit; and
a display control unit that sets an emphasized region having a larger area than the region of interest and including the region of interest and that displays the emphasized region in the medical image in a manner of emphasized display,
wherein the display control unit determines whether or not to change setting of the emphasized region in accordance with an amount of variation of the region of interest in the medical image,
wherein the display control unit sets a reference region on an outer side of the region of interest and an inner side of the emphasized region when setting the emphasized region, and resets the emphasized region and the reference region in a case where at least a part of the region of interest has shifted to an outside of the reference region, and
wherein the display control unit does not reset the emphasized region and the reference region in a case where the region of interest has shifted within the reference region.

2. The medical image processing apparatus according to claim 1, wherein in a case of resetting the emphasized region and the reference region after setting the emphasized region and the reference region, the display control unit causes a position of the emphasized display after resetting to be different from a position of the emphasized display before resetting.

3. The medical image processing apparatus according to claim 1, wherein in a case of resetting the emphasized region and the reference region after setting the emphasized region and the reference region, the display control unit causes the emphasized display after resetting to be enlarged relative to the emphasized display before resetting.

4. The medical image processing apparatus according to claim 1, wherein in a case where an enlargement ratio of an area of the region of interest exceeds a first threshold value after the emphasized region is set, the display control unit resets the emphasized region to cause the emphasized display after resetting to be enlarged relative to the emphasized display before resetting.

5. The medical image processing apparatus according to claim 4, wherein in a case where the enlargement ratio of the area of the region of interest exceeds a second threshold value greater than the first threshold value after the emphasized region is set, the display control unit makes a change to reduce an area of a figure to be superimposed on the medical image for the emphasized display.

6. The medical image processing apparatus according to claim 5, wherein in a case where the enlargement ratio exceeds the second threshold value, the display control unit causes an icon or a band-shaped figure to be displayed outside a part to be observed in the medical image for the emphasized display.

7. The medical image processing apparatus according to claim 1, wherein the display control unit determines representative coordinates of the region of interest detected by the region-of-interest detecting unit, and resets a position of the emphasized region in a case where a position of the representative coordinates has moved by a threshold value or more.

8. The medical image processing apparatus according to claim 1, wherein the display control unit causes a frame-shaped figure superimposed on the emphasized region to be displayed for emphasized display.

9. The medical image processing apparatus according to claim 1, wherein the display control unit changes a color of the emphasized region to a color different from a color of an other portion of the medical image for emphasized display.

10. An endoscope system comprising:
   a light source device that emits illumination light for illuminating an observation target;
   an endoscope having an imaging device that performs imaging of the observation target illuminated with the illumination light;
   a processor configured to function as:
      a medical image acquiring unit that acquires a medical image, the medical image being obtained through imaging of the observation target performed by the imaging device;
      a region-of-interest detecting unit that detects a region of interest in the observation target from the medical image acquired by the medical image acquiring unit;
      a display control unit that sets an emphasized region having a larger area than the region of interest and including the region of interest and that displays the emphasized region in the medical image in a manner of emphasized display,
         wherein the display control unit determines whether or not to change setting of the emphasized region in accordance with an amount of variation of the region of interest in the medical image,
            wherein the display control unit sets a reference region on an outer side of the region of interest and an inner side of the emphasized region when setting the emphasized region, and resets the emphasized region and the reference region in a case where at least a part of the region of interest has shifted to an outside of the reference region, and
            wherein the display control unit does not reset the emphasized region and the reference region in a case where the region of interest has shifted within the reference region; and
   a display device that displays the medical image to which the emphasized display is applied.

11. A method for operating a medical image processing apparatus, comprising following steps performed by a processor:
   acquiring a medical image, the medical image being obtained through imaging of an observation target performed by an imaging device;
   detecting a region of interest in the observation target from the medical image;
   setting an emphasized region having a larger area than the region of interest and including the region of interest;
   displaying the emphasized region in the medical image in a manner of emphasized display;
   determining whether or not to change setting of the emphasized region in accordance with an amount of variation of the region of interest in the medical image;
   setting a reference region on an outer side of the region of interest and an inner side of the emphasized region when setting the emphasized region, and resetting the emphasized region and the reference region in a case where at least a part of the region of interest has shifted to an outside of the reference region; and
   not resetting the emphasized region and the reference region in a case where the region of interest has shifted within the reference region.

* * * * *